United States Patent [19]

Magruder et al.

[11] Patent Number: 5,180,591
[45] Date of Patent: Jan. 19, 1993

[54] DELIVERY DEVICE WITH A PROTECTIVE SLEEVE

[75] Inventors: Judy A. Magruder, Mountain View; John R. Peery, Palo Alto; James B. Eckenhoff, Los Altos, all of Calif.

[73] Assignee: Alza Corporation, Palo Alto, Calif.

[21] Appl. No.: 551,720

[22] Filed: Jul. 11, 1990

[51] Int. Cl.$^5$ ............................................... A61K 9/24
[52] U.S. Cl. .................... 424/473; 424/422; 424/423; 424/438; 604/890.1
[58] Field of Search ............... 424/473, 422, 423, 438; 604/890.1

[56] References Cited

U.S. PATENT DOCUMENTS

| | | | |
|---|---|---|---|
| 2,779,241 | 6/1954 | Howard | 89/1 |
| 3,732,865 | 5/1973 | Higuchi et al. | 128/260 |
| 3,845,761 | 11/1974 | Zaffaroni | 128/130 |
| 3,845,770 | 11/1974 | Theeuwes et al. | 128/260 |
| 3,854,480 | 12/1974 | Zaffaroni | 128/260 |
| 3,865,108 | 2/1975 | Hartop | 128/260 |
| 3,896,819 | 7/1975 | Zaffaroni | 128/130 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes | 128/260 |
| 4,111,203 | 9/1978 | Theeuwes | 128/260 |
| 4,160,020 | 1/1979 | Ayer et al. | 424/15 |
| 4,200,098 | 11/1980 | Ayer et al. | 128/260 |
| 4,203,439 | 5/1980 | Theeuwes | 128/260 |
| 4,207,893 | 6/1980 | Michaels | 128/260 |
| 4,235,236 | 11/1980 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,320,759 | 3/1982 | Theeuwes | 128/260 |
| 4,327,725 | 5/1982 | Cortese et al. | 128/260 |
| 4,526,938 | 7/1985 | Churchill et al. | 525/415 |
| 4,612,008 | 9/1986 | Wong et al. | 604/892 |
| 4,855,141 | 8/1989 | Eckenhoff et al. | 424/423 |
| 4,874,388 | 10/1989 | Wong et al. | 604/891.1 |
| 4,969,884 | 11/1990 | Yum | 604/892.1 |
| 5,034,229 | 7/1991 | Magruder et al. | 424/422 |
| 5,057,318 | 10/1991 | Magruder | 424/438 |
| 5,059,423 | 10/1991 | Magruder | 424/438 |

FOREIGN PATENT DOCUMENTS

373867  6/1990  European Pat. Off. .

*Primary Examiner*—Thurman K. Page
*Assistant Examiner*—D. Gabrielle Phelan
*Attorney, Agent, or Firm*—Jacqueline S. Larson; Edward L. Mandell; Steven F. Stone

[57] ABSTRACT

This invention relates to an active agent delivery device. More particularly, the invention relates to a delivery device that includes a sleeve to protect the delivery device from transient mechanical forces. The delivery device of the invention is robust and resistant to transient mechanical forces. The invention provides a fluid-imbibing delivery device comprising a housing enclosing an internal compartment, said housing having a first wall section that substantially restricts the passage of fluid into the delivery device, i.e. is substantially fluid-impermeable, and that contains a beneficial agent; a second wall section that permits the passage of fluid into the delivery device, i.e. is fluid-permeable, and that contains at least one expandable driving member; and exit means; with a protective sleeve means extending from the first wall section of the housing to cover and protect the second wall section of the housing and the junction of the first and second sections. The protective sleeve is preferably configured to provide substantially no resistance to flow of fluid or fluid vapors through the fluid-permeable second wall section.

6 Claims, 4 Drawing Sheets

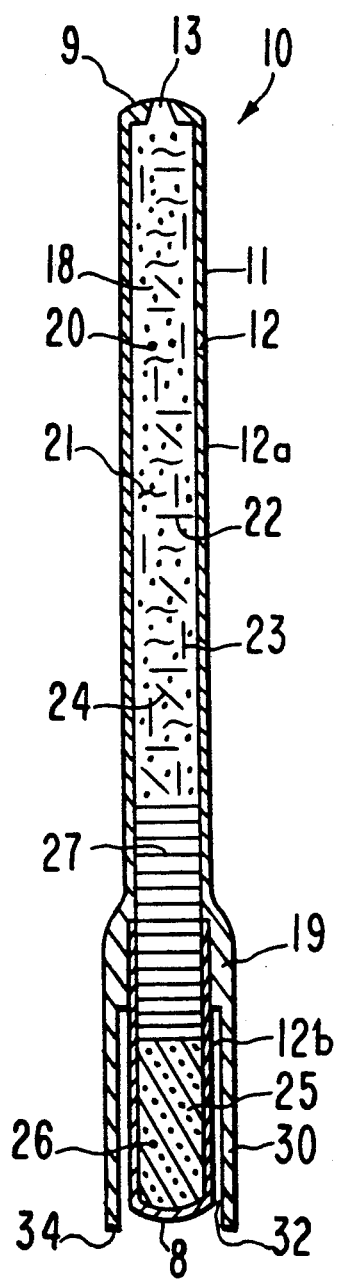
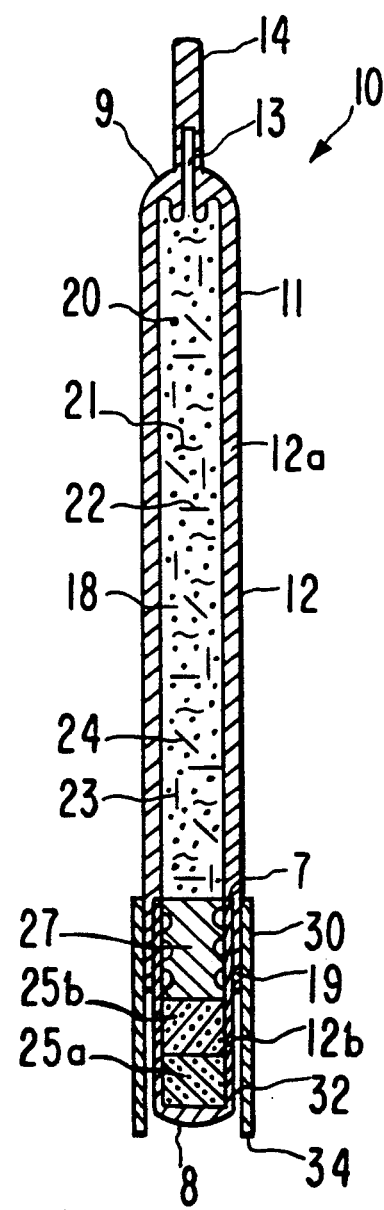

DELIVERY DEVICE WITH A PROTECTIVE SLEEVE

FIELD OF THE INVENTION

This invention relates to an active agent delivery device. More particularly, the invention relates to a delivery device that is robust and resistant to transient mechanical forces.

BACKGROUND OF THE INVENTION

Delivery devices for administering a beneficial agent to a biological fluid environment of use are known in the prior art. Representative examples of various types of delivery devices are disclosed in U.S. Pat. Nos. 3,845,770; 3,916,899; 3,995,632; 4,111,202; 4,111,203; 4,203,439; 4,327,725; and 4,612,008, which are incorporated herein by reference. The delivery devices described in the above patents operate successfully for their intended use and they can deliver many beneficial agents for their intended effects. However, it has been observed that their use can be limited because they lack the necessary elements to deliver beneficial agents that are sensitive to fluids and to fluids containing biological gases. Their use may be limited because beneficial agents that are sensitive to such aqueous biological fluids or to other fluids external to the delivery device may be adversely affected by fluids that enter the device and contact the beneficial agents during operation of the device. Examples of such fluid-sensitive agents include proteins, peptides, and hormones. Moreover, the prior art devices lack the necessary means for their use as implant devices for dispensing such sensitive agents to a biological fluid-rich environment of use.

To overcome the limitations associated with the prior art delivery devices, a delivery device has been developed and is described and claimed in commonly-assigned U.S. Pat. No. 5,034,229, filed Dec. 13, 1988, to Magruder et al. for Delivery System Comprising Means for Governing Fluid Ingress into the System, the entire disclosure of which is incorporated herein by reference. This delivery device comprises a compartment, one portion of which is impermeable to fluid and contains a fluid-sensitive drug protected from a fluid environment and a second portion of which is permeable to fluid and contains an expandable driving member for administering the drug to the fluid environment of use. The system has been found to be particularly useful as an implant in livestock for delivering a fluid-sensitive drug over a broad range of dosage delivery rates according to a predetermined time-release pattern.

Although in vitro tests and in vivo tests on isolated animals indicated satisfactory system performance, in vivo tests under field conditions of the delivery device of U.S. Pat. No. 5,034,229 in livestock demonstrated an undesirably high failure rate, either by failing to deliver the beneficial drug at the desired rates or by failing to deliver the required dosage of the drug or by the fluid-sensitive drug coming into contact with fluid prematurely and becoming adversely affected prior to its delivery into the fluid environment of the host animal. The discrepancy between in vivo tests on isolated animals and on animals under field conditions was totally unexpected, not readily explained, and could adversely affect the commercialization of the delivery device.

SUMMARY OF THE INVENTION

It has now been discovered by the inventors that the failure of the devices of U.S. Pat. No. 5,034,229 under field conditions was attributable to damage to the portion of the compartment containing the expandable driving member or damage to the junction between the permeable and impermeable portions of the compartment as a result of radially applied transient mechanical forces, which forces are the result of such actions as the implant procedure itself; behavior patterns of the host animals, such as animal-to-animal interaction which is often violent, and collisions of the animals into guardrails of pens or other structures; and miscellaneous in vivo forces which act upon the implanted delivery device. It was also discovered that the frequency of failure could be greatly reduced if these delivery devices were rendered more robust and resistant to such transient mechanical forces in a manner that does not interfere with delivery of the protected beneficial agent at a controlled rate.

Accordingly, it is desirable to provide a delivery device that is robust and resistant to mechanical forces in vivo and does not interfere with the in vivo delivery of a beneficial agent.

Therefore, the present invention provides a fluid-imbibing delivery device comprising a housing enclosing an internal compartment, said housing having a first wall section that substantially restricts the passage of fluid into the delivery device, i.e. is substantially fluid-impermeable, and that contains a beneficial agent; a second wall section that permits the passage of fluid into the delivery device, i.e. is fluid-permeable, and that contains at least one expandable driving member; and exit means; with a protective sleeve means extending from the first wall section of the housing to cover and protect the second wall section of the housing and the junction of the first and second sections. The protective sleeve is preferably configured to provide substantially no resistance to flow of fluid or fluid vapors through the fluid-permeable second wall section.

It has now been found that the placement of a protective sleeve of sufficient strength onto the delivery device of U.S. Pat. No. 5,034,229 and extending from the substantially impermeable first wall section of the device over and around the sides of the water-permeable second wall section and over the junction of the two wall sections provides sufficient protection to the delivery device so that the device does not break or otherwise become nonfunctional or malfunctional as a result of transient mechanical forces.

The protective sleeve of the present invention is of a sufficiently high tensile strength and rigidity to resist transient mechanical forces of about two kilograms or more. The inside diameter of the sleeve is greater than the outside diameter of the permeable portion of the compartment to allow access of environmental fluids or fluid vapors to the surface area of the permeable compartment portion. The sleeve may be integral with the first wall section or it may be a separate entity that is attached to the first wall section. The length of the sleeve may extend to cover in part or totally the sides of the second wall section. The sleeve may further comprise a plurality of fluid or fluid vapor passage means which facilitate ventilation of air from the annular space between the sleeve and the permeable portion of the compartment wall during the implant procedure and

3 which facilitate access of the environmental fluid to the permeable wall.

BRIEF DESCRIPTION OF THE DRAWINGS

FIG. 1 is an opened view of one embodiment of the delivery device of the invention, illustrating one structural embodiment of the delivery system comprising a first walled section and a second walled section, where the sleeve of the invention extends from and is integral with the first walled section to protectively cover the second walled section.

FIG. 2 is an opened view of another embodiment of the delivery device of the invention, depicting a delivery system comprising a beneficial agent section and a driving member section joined as engaging structural member sections with a separate sleeve section extending from the beneficial agent section to protectively cover the driving member section and the junction of the two sections.

DETAILED DESCRIPTION OF THE INVENTION

Figure 3:
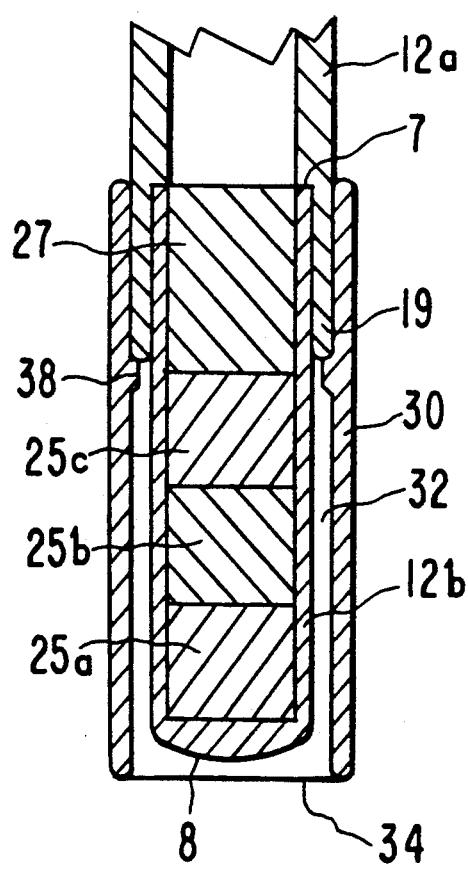
FIG. 3 is a partial opened view of a delivery device of the invention showing in greater detail the protective sleeve section in relation to the beneficial agent section and the driving member section of the device.

In the following discussion, like reference numerals refer to like elements in the figures.

FIG. 1 depicts in opened view one embodiment of the delivery device according to the present invention. Delivery system 10 of FIG. 1 comprises a housing 11 formed of a wall 12, which wall 12 comprises a first wall section 12a and a second wall section 12b. Wall 12, comprising first wall section 12a and second wall section 12b, surrounds and defines an internal compartment 18. Delivery system 10 has at least one exit passageway 13 for deliverying a beneficial agent formulation from delivery system 10. Optionally, the exit passageway can be occluded with a material that gets discharged, leaches or erodes during the time of use. In FIG. 1, delivery system 10 comprises a dome-shaped rear end 8 and a similar dome-shaped lead end 9 for aiding in placing delivery system 10 in an animal host. In an embodiment not shown, delivery system 10 can be manufactured with a pair of flat ends 8 and 9. The term "lead end", as used herein, generally denotes the end from which beneficial agent is released from the system. In use, either the lead end or the rear end may be implanted first. Delivery system 10 also comprises a rigid protective sleeve 30 surrounding a portion of housing 11 adjacent to rear end 8; sleeve 30 may, optionally, extend below rear end 8. Wall section 12a defines lead end 9, it forms passageway 13 and it surrounds that portion of internal compartment area 18 that contains a beneficial agent formulation. Wall section 12a at its end distant from lead end 9 defines and forms receiving means 19 and protective sleeve 30. Receiving means 19 is enlarged slightly for receiving second wall section 12b. Protective sleeve 30 is tubular in shape with an opening 34 and extends from the receiving means 19 down to cover the sides of second wall section 12b, providing a space 32 that is defined by the inner wall surface of sleeve 30 and the outer surface of wall 12b and is open to the environment at opening 34. Wall section 12b surrounds that portion of internal compartment area 18 that contains a means for expanding and for occupying space in compartment 18 for delivery of a beneficial agent formulation from delivery system 10. The two wall sections, sections 12a and 12b, at receiving means 19 are close in size and they form a tight friction fit therebetween. There is clearance or tolerance in size to allow wall section 12b a sliding movement into the receiving means 19 of wall section 12a. Wall section 12a and wall section 12b can be telescoped completely into a closed and continuous internal walled position. Optionally, they can be held together by heat fusion, by an adhesive, or the like.

First wall section 12a comprises a composition that is substantially impermeable to the exchange of fluid, beneficial agent and other ingredients contained in delivery system 10. Wall section 12a, in a presently preferred manufacture, is substantially impermeable to the ingress of an external fluid to serve as a means for substantially protecting a beneficial agent that is sensitive to fluid from an exterior fluid present in the environment of use. Wall section 12a substantially restricts and prevents fluid from passing through wall 12a and entering into compartment 18 in the region containing a beneficial agent formulation. Furthermore, wall section 12a, at least in the area comprising the protective sleeve 30, is of a composition that has an adequate tensile strength, thickness and rigidity to withstand transient mechanical forces in excess of about 2 kg$_f$ in order to protect wall section 12b and the junction of sections 12a and 12b at receiving means 19 from such forces. Second wall section 12b is permeable to the passage of fluid and it is substantially impermeable to the passage of other ingredients contained in delivery system 10. Wall sections 12a and 12b optionally comprise a plasticizer that imparts flexibility and workability to the wall. Wall 12, comprising sections 12a and 12b, is nontoxic and, in a preferred embodiment, it maintains its physical and chemical integrity; that is, wall 12 does not erode during the dispensing period.

Compartment 18 comprises a beneficial agent formulation, which beneficial agent formulation comprises a beneficial agent 20, identified by dots, and a pharmaceutically acceptable carrier 21, identified by wavy lines. The pharmaceutically acceptable carrier in one presently preferred embodiment comprises more than one ingredient, such as a buffer 22, identified by horizontal dashes; a pharmaceutically acceptable vehicle 23, identified by vertical lines; a pharmaceutically acceptable surfactant 24, identified by slanted lines; and other formulation ingredients, as are known in the art. Compartment 18 further comprises an expandable driving member 25, identified by slanted lines. Expandable driving member 25 optionally comprises an osmagent 26, identified by dots, homogeneously or heterogeneously blended with expandable driving member 25. Compartment 18 optionally comprises a partition layer 27, represented by horizontal lines, which layer 27 is positioned between the beneficial agent formulation and the expandable driving member 25. Partition layer 27, in a presently preferred embodiment, comprises a composition that is substantially impermeable to the passage of fluid, and it serves to restrict the passage of fluid present in the expandable driving member into the beneficial agent formulation. It operates to essentially maintain the integrity of the beneficial agent layer and the driving member layer. Partition layer 27 acts also to insure that the expanding driving force generated by the expandable driving member 25 is applied directly against the beneficial agent formulation. In operation, as the expandable member 25 absorbs and imbibes fluid through second wall section 12b from the environment of use, it expands and pushes against partition layer 27, causing it to slide inside compartment 18. Partition layer 27 moves towards exit passageway 13, pushing the beneficial agent formulation through passageway 13 for maximizing the delivery of the beneficial agent to a biological environment of use, such as livestock.

FIG. 2 is in opened view another embodiment of the delivery device of the invention. In FIG. 2, delivery device 10 comprises housing 11 formed by wall 12. Wall 12 comprises a first wall section 12a of fluid-impermeable composition that surrounds that portion of internal compartment 18 containing a beneficial agent, and a second wall section 12b of fluid-permeable composition that surrounds that portion of internal compartment 18 containing at least one means for expanding and for occupying space in the compartment for delivery of the beneficial agent. First wall section 12a is provided with receiving means 19, and second wall section 12b is provided with an opened end 7. First wall section 12a is thinner at receiving means 19 to provide an enlarged open end for slipping over or receiving second section 12b at its opened end 7, so that second wall section 12b is telescopically capped by the engaging first wall section 12a. The two sections can be joined together by various techniques such as solvent weld, adhesive bond, thermal weld, ultrasonic weld, spin weld, induction weld, or by similar welding or bonding operations.

Delivery system 10 also comprises protective sleeve 30 which is joined with first wall section 12a at a position over the junction of wall sections 12a and 12b at receiving means 19. Sleeve 30 is tubular in shape with an opening 34 and extends over and around the sides of second wall section 12b. The inner diameter of sleeve 30 is greater than the outer diameter of second wall section 12b to provide a space 32. Space 32 allows fluid or fluid vapor from the environment of use to come into contact with fluid-permeable second wall section 12b. Protective sleeve 30 should be of a material having a sufficiently high tensile strength, thickness and rigidity to withstand transient mechanical forces in excess of about two kg/in order to protect second wall section 12b and the junction of sections 12a and 12b at receiving means 19 from such forces. Rigid protective sleeve 30 can be joined to first wall section 12a by various techniques such as solvent weld, adhesive bond, thermal weld, ultrasonic weld, spin weld, induction weld, or by similar welding or bonding operation.

Delivery device 10 in FIG. 2 further comprises lead end 9, rear end 8, internal compartment 18, beneficial agent 20, pharmaceutically acceptable carrier 21, pharmaceutically acceptable buffer 22, pharmaceutically acceptable vehicle 23, and a pharmaceutically acceptable surfactant 24. In a presently preferred embodiment, delivery device 10 comprises a plurality of expandable driving members 25a and 25b initially housed in second wall section 12b. This configuration is merely illustrative and there may be any number of driving members present. Generally, there are from one to five expandable driving members; however, this number is not controlling. The expandable driving members in a presently preferred embodiment are formed as depots or layers and comprise like or unlike compositions. For example, driving members 25a and 25b can be made as tablets comprising like osmopolymers or like osmagents, or they can comprise unlike osmopolymers or unlike osmagents, or one or more of the members can be a composition comprising an osmopolymer together with an osmagent. The members can be the same or they can be different. The driving members can be inserted through open end 7 successively into second wall section 12b. Delivery device 10 in a presently preferred manufacture comprises partition layer 27 that separates the beneficial agent formulation from the expandable driving members, partition layer 27 being positioned at the time of manufacture near receiving means 19 of first wall section 12a.

In FIG. 2, delivery device 10 further comprises break-off or severable tab 14 at lead end 9. Break-off or severable tab 14 covers exit passageway 13. Tab 14 serves several purposes: it seals delivery device 10 to prevent premature delivery of a beneficial agent from delivery device 10, it helps maintain the clean or optionally sterile environment inside delivery device 10, and it protects the ingredients inside the delivery device from oxidation by air. Break-off tab 14 comprises an optional scored line (not shown) to enhance its separation from the delivery device. Tab 14 is easily snapped off at the time of use by manual pressure, by tapping, by twisting, by filing, by cutting, or the like, to provide an exit passageway. The break-off tab 14 can be formed during manufacture or it can be joined to the housing 11 by heat fusion, adhesive joining or the like. Optionally in combination with break-off tab 14, the exit passageway can be occluded with material that gets discharged, leaches or erodes during the time of use.

In one embodiment of delivery device 10 as illustrated in FIG. 2, the system is manufactured as an implant comprising a body length of about 49.68 mm, a diameter of the first wall section of about 4.97 mm, a diameter of the second wall section of about 4.09 mm, a diameter of the protective sleeve of about 5.97 mm, a sleeve wall thickness of about 0.51 mm, a beneficial agent formulation occupying a length of 33.73 mm, a partition layer occupying a space of 5.08 mm, and an initial total space of 7.62 mm occupied by the expandable driving members. The optional break-off tab is about 6.35 mm in length and when broken off forms an exit passageway of 0.51 mm. Prior to placement in the receiving tissue, the break-off tab can be broken off and the exit passageway can be occluded with a material such as wax that gets discharged, leaches or erodes when placed in the tissue. The implant can be implanted into receiving tissue using an implanter. Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Also, the implant can be surgically implanted in the muscle or other tissue of livestock.

Figure 4:
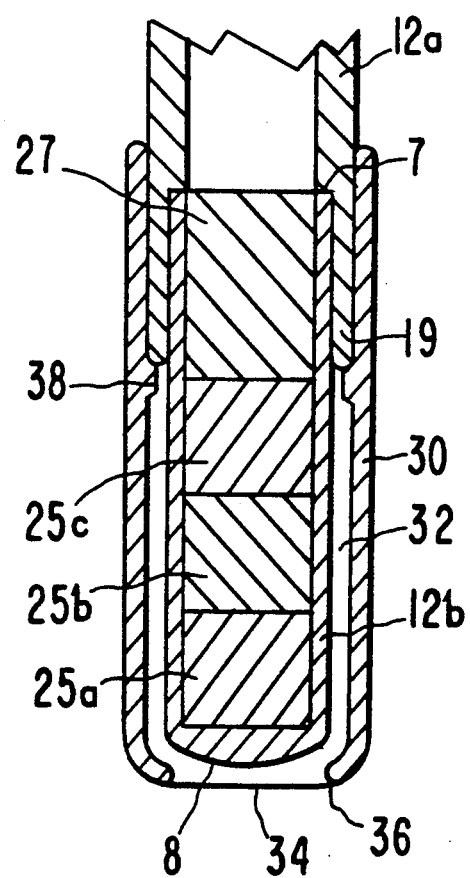
FIG. 4 is a partial opened view of another delivery device of the invention.

FIGS. 3 and 4 are opened views of that portion of delivery device 10 encompassing the rigid protective sleeve 30, shown in greater detail. Sleeve 30 is tubular in shape and is joined with first wall section 12a to cover the junction of first wall section 12a and second wall section 12b at receiving means 19. While sleeve 30 can cover only a portion of the junction between the first and the second wall sections, in a presently preferred embodiment, as illustrated in FIG. 3, sleeve 30 extends to cover the entire thinner portion of first section 12a, that is, that portion comprising receiving means 19 that slips over or receives open end 7 of second section 12b. Sleeve 30 can optionally extend to cover a portion of first section 12a beyond the thinner section, as illustrated in FIG. 4. In this manner, the junction between first section 12a and second section 12b, which has been found by the inventors to be a point of weakness in the delivery system, is reinforced by protective sleeve 30 against transient mechanical forces to prevent breakage of the delivery system at this point. Protective sleeve 30 and first wall section 12a can be joined together by various techniques such as solvent weld, adhesive bond, thermal weld, ultrasonic weld, spin weld, induction weld, or by similar welding or bonding operations known in the art.

Tubular protective sleeve 30 extends down from receiving means 19 of first section 12a to rear end 8 of delivery device 10, thus surrounding the sides of second wall section 12b and protecting the wall section from damage as a result of transient mechanical forces. The sleeve can extend just tot he end of rear end 8, or it can stop a short distance above rear end 8, or preferably it extends slightly below rear end 8 as illustrated in FIGS. 3 and 4. In a preferred embodiment, the length of sleeve 30 coincides with the end of rear end 8 when rear end 8 has undergone the expansion that often occurs as a result of fluid imbibition. The protective sleeve 30 may optionally be radiused or contoured to form a lip 36, as illustrated in FIG. 4, to partially cover and enclose rear end 8. The inner diameter of the wall of sleeve 30 is greater than the outer diameter of second section 12b, forming a space 32 between the two walls. This space 32 is necessary for the proper functioning of the driving member or members, 25a, 25b and 25c for example, housed within second section 12b. In other words, space 32 allows fluid or fluid vapor from the environment of use to come into contact with the fluid-permeable wall of second section 12b through opening 34 of sleeve 30 in order to activate the driving members. Space 32 should be of sufficient width to allow an adequate supply of fluid or fluid vapor to come into contact with second section 12b along its entire surface area. The width of the space 32 between sleeve 30 and second section 12b is, in a presently contemplated embodiment, minimally about 0.0020 in. (0.051 mm) and preferably about 0.020 in. (0.51 mm).

Figure 5:
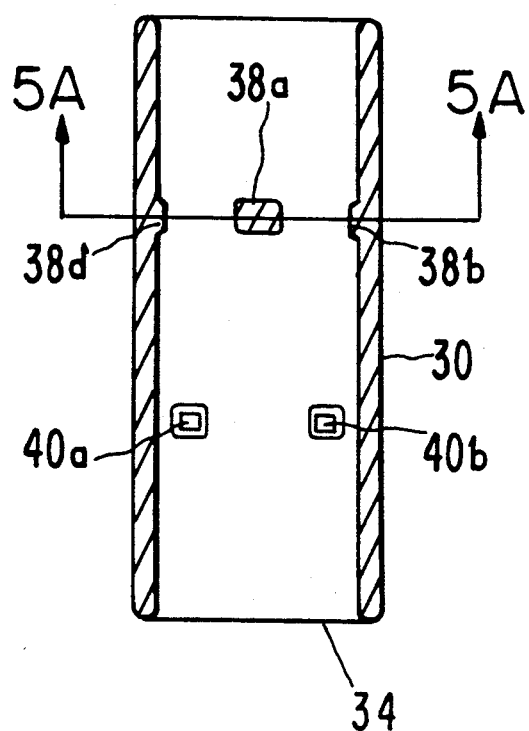
FIG. 5 is an opened view of a protective sleeve of the present invention prior to installation on a delivery device.
Figure 5A:
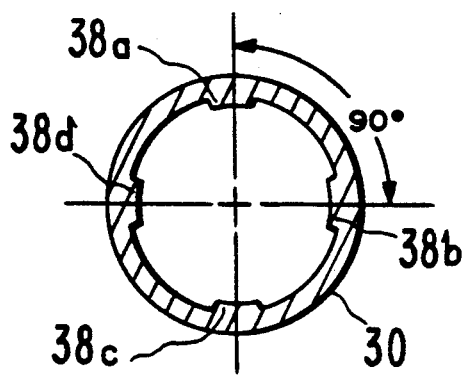
FIG. 5A is a cross-sectional view through line A—A of the protective sleeve of FIG. 5.

In a presently preferred embodiment where protective sleeve 30 is a separate entity from and not integral with first wall section 12a, protective sleeve 30 comprises a ridge or ridges 38 on the inner wall surface of the sleeve, as shown in FIGS. 3 and 4. This ridge 38 can be continuous, extending around the entire inner circumference of sleeve 30, or there can be a plurality of individual ridges spaced at intervals in the same plane around the inner circumference of sleeve 30, such as ridges 38a, 38b, 38c and 38d as illustrated in FIGS. 5 and 5A. Ridge or ridges 38 are located in sleeve 30 so that, in the completed delivery device, they rest against the end of receiving means 19 of first wall section 12a at a point so that a portion of sleeve 30 extends to cover the junction of first wall section 12a and second wall section 12b and the remainder of sleeve 30 extends around the sides of second wall section 12b. While they are not necessary to the protective function of the sleeve, ridge or ridges 38 assist in the manufacturing process by providing a stop against receiving means 19 when sleeve 30 is slipped onto wall section 12a, and they can provide additional stability to the delivery device.

Figure 6:
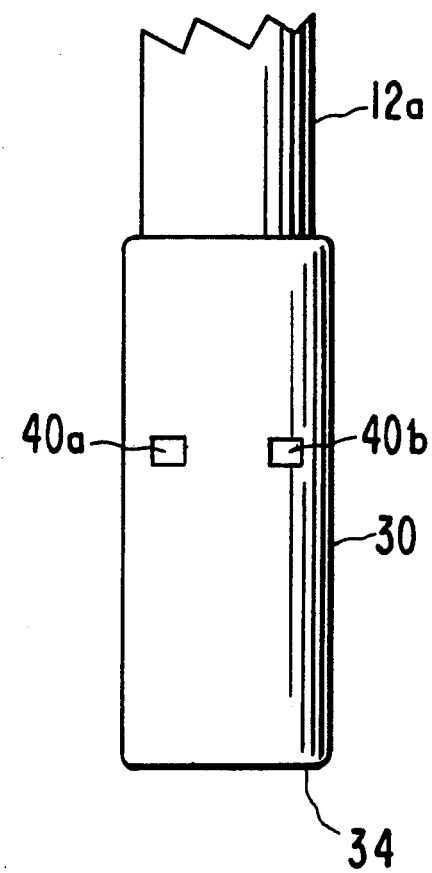
FIG. 6 is a partial exterior view of a delivery device of the invention showing a protective sleeve of the present invention.

In a presently contemplated embodiment of the invention, protective sleeve 30 further comprises one or a plurality of fluid or fluid vapor passage means, shown as holes 40a and 40b in FIGS. 5 and 6, through the wall of the sleeve, which holes communicate with the outside environment of use and with space 32 between sleeve 30 and second section 12b. These holes facilitate ventilation of air from space 32 during the implant procedure and provide another point of access to second section 12b for the fluid or fluid vapor environment. The holes are preferably placed relatively closer to receiving means 19 than to sleeve opening 34.

Figure 7:
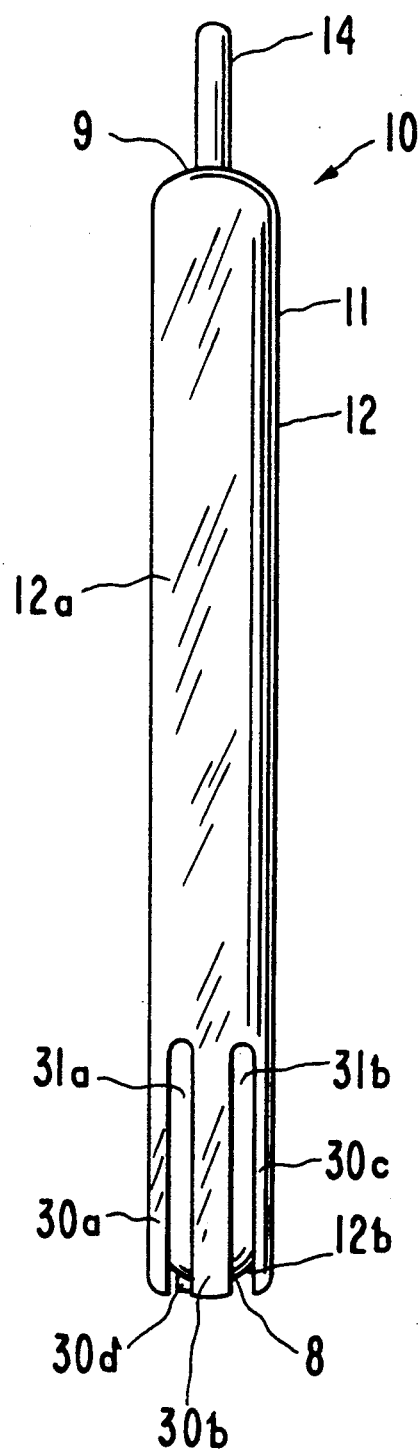
FIG. 7 is an exterior view of another delivery device of the invention wherein the delivery device includes a protective sleeve comprising a plurality of ribs.

FIG. 7 shows an alternative embodiment of delivery device 10 of the present invention. As seen in FIG. 7, system 10 comprises a housing 11 formed of a wall 12 with a rear end 8 and lead end 9 with break-off tab 14. Wall 12 comprises a first wall section 12a and a second wall section 12b. First wall section 12a has formed integrally therewith a protective sleeve 30 which comprises a plurality of ribs 30a, 30b, 30c and 30d extending down over second wall section 12b and separated from each other by longitudinal spaces 31a, 31b, 31c and 31d (of which, 31a and 31b are shown). These ribs, 30a for example, provide protection from transient mechanical forces for second wall section 12b while the longitudinal spaces, 31a for example, allow the passage of fluid from the environment to come into contact with second wall section 12b. The ribs, 30a for example, of the protective sleeve extend from the receiving means 19 (not shown) down to cover second wall section 12b, providing a space 32 that is defined by the inner wall surface of the sleeve ribs, 30a for example, and the outer surface of wall 12b and is open to the environment at opening 34 and through longitudinal spaces 31a–31d.

In accordance with the practice of this invention, it has now been found that device 10 can be manufactured with a rigid protective sleeve 30 that at least partially surrounds the sides of second wall section 12b and the junction of second wall section 12b and first wall section 12a. Protective sleeve 30 comprises a composition that is nontoxic to animals and livestock and is compatible with the environment of use. The material comprising sleeve 30 is of a high tensile strength and a sufficient thickness to withstand transient mechanical forces. It has been found that the devices of U.S. Pat. No. 5,034,229, without the protective sleeve of this invention, tend to become malfunctional or nonfunctional when a transient mechanical force of about 2 kg$_f$ is radially applied to the junction of the water-impermeable and the water-permeable wall portions. Therefore, it is necessary that the protective sleeve be comprised of a material of a strength sufficient to withstand transient mechanical forces of at least about 2 kg$_f$ and preferably of at least about 6 kg$_f$ of force. Usually, a material having a minimum tensile strength at yield of about 9,000 psi is acceptable for use in the present invention. The tensile strength may be lower, in which case the sleeve wall is thicker to provide the necessary strength.

While the composition of the sleeve 30 may be of a semipermeable material, so long as the material is of sufficient strength as required herein, in a presently preferred embodiment the composition is of a material which is substantially impermeable to fluids. Typical impermeable compositions for forming protective sleeve 30 are vinylidene chloride copolymers and terpolymers such as vinylidene chloride-vinyl chloride copolymer, vinylidene chloride-acrylonitrile copolymer, vinylidene chloride-styrene copolymer, and vinylidene chloride-vinyl chloride-acrylonitrile terpolymer; acrylonitrile polymers such as acrylonitrile-methyl vinyl ether copolymer, acrylonitrile-styrene copolymer, acrylonitrile-butadiene-styrene terpolymer, and the like; halogenated polymers such as chlorinated polyether, polytetrafluoroethylene, polychlorotrifluoroethylene, tetrafluoroethylene and hexafluoropropylene copolymer, polyvinylfluoride, polyvinylchlorobuteral, plasticized polyvinylidene chloride, and the like; nylon; polyamide-imide; polyarylether; polysulfone; polycarbonate; polyurethane; high density polyethylene; polyvinylchloride-acrylic copolymer; polycarbonate-acrylonitrile-butadiene-styrene; glass; bakelite; melamine; polystyrene, polyacrylate; stainless steel and stainless steel mesh; and the like. Polycarbonate and polysulfone are presently preferred. The polymers are known in the *Handbook of Common Polymers*, by Scott and Roff, CRC Press, Cleveland Rubber Co., Cleveland, Ohio. When the composition of sleeve 30 comprises a semipermeable material, the semipermeable material may be strengthened by the addition of rigid fillers, such as glass or ceramic, for example.

First wall section 12a, which surrounds the internal space of compartment 18 initially occupied by the beneficial agent formulation, comprises a composition that does not adversely affect the beneficial agent, the osmopolymer, the osmagent, other ingredients in device 10, the host, or the like. First wall section 12a comprises a composition comprising means that substantially limits or prevents the passage of an external fluid into device 10. The phrase, "substantially limits or prevents," as used herein, indicates the volume of external fluid passing through first wall section 12a is substantially negligible, that is, about zero up to about 1 µl per day. Typical compositions for forming first section 12a are chosen from the substantially impermeable compositions listed above for protective sleeve 30 and may be the same as or different from the composition making up the protective sleeve.

The second wall section 12b comprises a composition comprising means that aids in controlling fluid flux into the compartment area occupied by the expandable driving member. The composition is permeable to the passage of external fluids such as water and biological fluids, and it is substantially impermeable to the passage of beneficial agents, osmopolymers, osmagents, and the like. Typical compositions comprising semipermeable materials for forming wall 12b are known in the art. In one presently preferred embodiment, they are a member selected from the group consisting of a cellulose ester, a cellulose ether and a cellulose ester-ether. These cellulosic polymers have a degree of substitution, D.S., on the anhydroglucose unit from greater than 0 up to 3, inclusive. By "degree of substitution" or "D.S." is meant the average number of hydroxyl groups originally present on the anhydroglucose unit comprising the cellulose polymer that are replaced by a substituting group. Representative fluid-permeable materials are discussed in U.S. Pat. No. 4,874,388, for example.

First wall section 12a, second wall section 12b and sleeve 30 optionally comprise a nontoxic plasticizer. Representative plasticizers suitable for forming wall 12a, wall 12b or sleeve 30 include plasticizers that lower the temperature of the second-order phase of transition or the elastic modulus of a composition. Also, the plasticizers increase the workability of wall 12a, wall 12b or sleeve 30 and their flexibility. Plasticizers operable for the present purpose include straight-chain and branched-chain plasticizers, cyclic plasticizers, acrylic plasticizers and heterocyclic plasticizers. Representative plasticizers are well known in the art.

Delivery device 10 in that portion of its compartment 18 surrounded by first wall section 12a comprises a beneficial agent 20 that produces a desired and useful result when administered to a warm-blooded animal, including humans and farm animals. The beneficial agent 20 is useful in one embodiment for increasing the rate of growth and the efficiency of feed utilization in equine, bovine and swine. The beneficial agent 20 in another embodiment is useful for controlling estrus and ovulation in the course of breeding farm animals for commercial purposes, for effecting contraception and for producing an anabolic response associated with the inhibition of estrus. Beneficial agent 20 in another embodiment is a drug useful for producing a therapeutic effect. The beneficial agent 20 in yet other embodiments comprises agents that act at synaptic and neuroeffector sites, agents acting on the central nervous system, autocoids, anti-inflammatory agents, analgesics, antipyretic agents, cardiovascular agents, and the like.

Representative beneficial agents 20 that can be administered by delivery device 10 include pharmacologically active peptides and proteins, anabolic hormones, growth promoting hormones, hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalmus glands, growth promoting hormones produces by recombinant DNA methods, bovine growth promoting hormone as described in *Nucleic Acid Res.*, 10:7197 (1982), ovine growth promoting hormone as described in *Arch. Biochem. Biophys.*, 156:493 (1973), and porcine growth promoting hormone as described in DNA, 2:37 (1983). The polypeptides also comprise growth hormone, somatropin, somatotropin, somatotropin analogues, modified porcine somatotropin, modified bovine somatotropin, derivatives of somatotropin including both porcine and bovine somatotropin derivatives, somatomedin-C, gonadotropic releasing hormone, follicle stimulating hormone, luteinizing hormone, LH-RH, growth hormone releasing factor, gonadotropin releasing factor, insulin, colchicine, chorionic gonadotoprin, oxytocin, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulating hormone, secretin, pancreozymin, enkephalin, glucagon, endocrine agents secreted internally and distributed in an animal by way of the bloodstream, and the like. The beneficial agents and their dosage unit amounts are known to the prior art in *The Pharmacological Basis of Therapeutics*, by Gilman, Goodman, Rall and Murad, 7th Ed., (1985), MacMillan Publishing Co., N.Y.; in *Pharmaceutical Sciences*, Remington, 17th Ed., (1985), Mack Publishing Co., Easton, Pa.; and in U.S. Pat. No. 4,526,938. Other useful beneficial agents are discussed in U.S. Pat. No. 4,874,388. Generally, the delivery device 10 comprises from about 5 nanograms to about 20 grams of beneficial agent 20.

Delivery device 10 in its compartment 18 can also comprise pharmaceutical carrier 21. Carrier 21 comprises beneficial agent 20 and also can comprise viscosity modulating vehicles, buffers, surfactants, dyes, and other additives known in the art.

The expandable driving means 25 initially surrounded by second wall section 12b and operable for pushing the beneficial agent composition 20 from delivery device 10 comprises, in a presently preferred embodiment, an osmopolymer. The osmopolymers interact with water and aqueous biological fluids and swell or expand to an equilibrium state. The osmopolymers exhibit the ability to swell in water and to retain a significant portion of the imbibed and absorbed water within the polymer structure. The expandable driving member 25 in another preferred embodiment comprises an osmagent. The osmagents are known also as osmotically effective solutes and they are also known as osmotically effective compounds. The osmotically effective compounds that can be used for the purpose of this invention include inorganic and organic compounds that exhibit an osmotic pressure gradient across a semipermeable, i.e. a fluid-permeable, wall. The expandable driving member 25 yet in another preferred embodiment comprises an optical osmagent dispersed within the osmopolymer. The osmagent or osmopolymer can comprise a tablet or a layer or can be pressed into second wall section 12b. The osmagent or osmopolymer can be in any suitable form such as particles, crystals, pellets, granules, and the like, when pressed into a tablet layer and into wall section 12b. Osmagents and osmopolymers are known to the art in U.S. Pat. Nos. 3,865,108, 4,002,173, 4,207,893, 4,327,725 and 4,612,008, for example.

Partition layer 27, positioned between the beneficial agent composition and the expandable driving member, is a means for maintaining the separate identity of the beneficial agent composition and the driving member, for transmitting the force generated by the driving member against the beneficial agent composition, and for substantially restricting the passage of fluid between the beneficial agent composition and the driving member. Representative materials useful as a partition layer 27 are known to the art in, for example, U.S. Pat. No. 4,874,388.

The terms "exit means" and "exit passageway", as used herein, comprise means and methods suitable for the metered release of the beneficial agent 20 from compartment 18 of delivery device 10. The exit means 13 includes at least one passageway, orifice, or the like, through first wall section 12a for communicating with compartment 18. The expression "at least one passageway" includes aperture, orifice, bore, pore, porous element through which the agent can migrate, hollow fiber, capillary tube, porous overlay, porous insert, and the like. The expression also includes material that gets discharged, erodes or is leached from the wall in the fluid environment of use to produce at least one passageway in delivery device 10. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid-removable pore-forming polysacharaides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. A passageway or passageways can be formed by the discharge, as a result of the pressure created by the expandable member for example, of a material such as a wax. The passageway can have any shape such as round, triangular, square, elliptical, and the like, for assisting in the metered release of beneficial agent from delivery device 10. Delivery device 10 can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,008,864. Passageways formed by leaching are disclosed in U.S. Pat. Nos. 4,200,098 and 4,285,987.

Delivery device 10 can be manufactured by standard manufacturing techniques. In one process, the first wall section 12a and the second wall section 12b are independently injection molded or extruded into the desired shape. Protective sleeve 30 can be manufactured as an integral part of first wall section 12a or, preferably, it is manufactured as a separate component by, for example, injection molding or extrusion in the same manner as the wall sections. Then, the first wall section 12a is filled with the beneficial agent composition. Then, the second wall section 12b is filled with an expandable driving member or members, and the partition layer is next added thereto in layered arrangement. Optionally, the partition layer may be added to the first wall section 12a after filling the wall section with beneficial agent, in addition to, or instead of, the partition layer added to second wall section 12b. Next, the two sections at their open ends are slid together. The union can be effected by having the opened end of one of the wall sections enlarged for slidably receiving the end of the other wall section in mated relation to form an essentially fluid-tight union. In another embodiment, the opened end of one of the wall sections is made smaller than the end of the other wall section, and the smaller end is placed in the non-enlarged end to form a closed system. The two wall sections at their junction are optionally heat sealed, adhesive sealed, solvent sealed, ultrasonically sealed, radiofrequency sealed, or spin welded, also known as friction heating to weld. When protective sleeve 30 is made as a component separate from first section 12a, it is then slipped over second wall section 12b and slid over first wall section 12a at the junction of sections 12a and 12b. Protective sleeve 30 and first wall section 12a are joined together by heat seal, adhesive seal, solvent seal, ultrasonic seal, radiofrequency seal, or spin weld, for example, Then, at least one passageway is drilled in the lead end of the manufactured assembly. Alternately, the exit passageway can be preformed, such as during the injection molding of first wall section 12a. Optionally, a passageway is drilled or preformed in the wall and sealed with a break-off tab that is broken open, or cut open, or the like, at the time of use to connect through the passageway the beneficial agent composition with the exterior of delivery device 10. Or, the drilled or preformed passageway is sealed by a material that gets discharged, leaches, erodes, or dissolves, for example, in the environment of use.

The delivery device of the present invention can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in beneficially effective amounts over time while providing resistance to transient mechanical forces. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous implant, and the like. The delivery devices can be used in hospitals, nursing homes, outpatient clinics, sickrooms, veterinary clinics, farms, zoos, and other environments of use.

One embodiment of the invention pertains to a method for delivering a beneficial agent such as a drug to an animal. The method comprises implanting a delivery device, shaped, sized and adapted as an implant, into an animal, such as a muscle or an ear thereof. The method comprises the steps of: (a) admitting into an animal a delivery device of the present invention; (b) allowing fluid to be imbibed through the semipermeable second wall section of the delivery device for causing the expandable driving means to expand and push against the beneficial agent formulation; and (c) delivering the beneficial agent formulation from the delivery device by the expandable means increasing in volume at a controlled rate, thereby pushing the beneficial agent formulation to be delivered in an effective amount through the exit orifice to the animal over a prolonged period of time.

DETAILED DESCRIPTION OF EXAMPLES

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A delivery device manufactured in the shape of an implantable delivery device comprising a lead end with an exit passageway and a distant rear end is manufactured as follows.

First, an expandable driving member is prepared by adding 7.6 kg of water and 0.4 kg of polyvinyl pyrrolidone to a stainless steel container and mixing the components for 20 hours to obtain a smooth binder solution. Next, 10.0 kg of sodium Carbomer ®, a sodium salt of polyacrylic acid polymer, is sized by forcing it through a 0.028 inch mesh screen in a fluid air mill set at 780–800 rpm speed. Next, 15.0 kg of sodium chloride is sized by forcing it through a 0.028 inch mesh screen in a fluid air mill set at 780–800 rpm speed. The 10 kg of screened polymer and the 15 kg of screened sodium chloride are transferred to the granulator bowl of a fluid bed granulator, and 6.13 kg of binder solution is slowly sprayed onto the polymer and the salt in the granulator. The polymer/salt granules are formed in this manner. These resultant granules are sized through a 16 mesh screen of a Sweco Separator. The amount of granulation from the above steps is 25.2 kg, and this is transferred to a blender. Then, enough magnesium stearate, a lubricant, is added to make up 1% of the total granulation including the lubricant. A total of 0.255 kg of magnesium stearate is added. All ingredients are mixed for three minutes at 10 rpm to produce a homogeneous expandable driving composition. The composition next is pressed into osmotically active tablets in a tablet press at a pressure of 500 lbs. to produce a round, flat-faced 50 mg tablet as an expandable driving member.

The semipermeable second wall section that surrounds a compartment for containing the osmotically active tablet is prepared as follows. First, 3.85 kg of cellulose acetate butyrate and 1.15 kg of tributyl citrate are dry blended in a mixer for 5 minutes. This produces a polymer plasticizer blend of 77/23 ratio for the rate-controlling semipermeable wall. The blend is then fed into an injection molder and molded into the semipermeable second wall section surrounding a compartment with an opened end for receiving an expandable driving member and for mating the second section with the lead, first wall section of the delivery device.

Next, the lead, impermeable first wall section of the delivery device is prepared by adding 5 kg of polycarbonate (Calibre ® 2000 series, Dow Chemical) to a hopper dryer and drying the polymer at 250° F. for 4 hours. Then, the dry polymer is fed into the hopper of an injection molder with a four-cavity subgated mold designed with an orifice in place and a break-off tab to open the orifice. This mold is used to injection-mold an impermeable first wall section surrounding a compartment with an open end for receiving components and for mating with the semipermeable second wall member. Next, the break-off tab is removed, and the orifice channel is sealed with wax in the following manner. First, 142 gm of microcrystalline wax 180M and 142 gm of microcrystalline wax X145A are weighed into a beaker on a hot plate to effect a 50/50 blend of the two waxes. The blend is then melted and heated and held to 105°–115° C. for the operation. The lead end (with the orifice channel) is dipped into the melted wax blend for 20 seconds, then removed from the melted wax and cooled for at least 20 seconds, and the excess wax is wiped off.

The protective sleeve is prepared by adding 5 kg of polycarbonate (Lexan ® HP 1, General Electric) to a hopper dryer and drying the polymer at 250° F. for 4 hours. The dry polymer is fed into a hopper dryer of an injection molder where a single-cavity hot tip mold is used to injection mold the protective sleeve with two open ends, one for mating with the fully assembled delivery device and the other to allow access of moisture to the semipermeable membrane area. There are also four ridges or stops spaced circumferentially around the inner wall of the sleeve.

Next, the elastomeric partition or piston is prepared by injection molding Santoprene ®, a thermoplastic elastomer, into a four-ribbed piston, weighing approximately 31 mg. Then, the piston is lubricated with silicone medical fluid 1000 cs to facilitate movement of the piston inside the device.

The delivery device is assembled by first charging the subassembly comprising the semipermeable second wall member with two of the osmotic tablets. Then, the lubricated elastomeric piston is inserted on top of the osmotic tablets to be flush with the top of the semipermeable walled member. Next, the delivery device subassembly comprising the substantially fluid-impermeable first wall member is filled with 340 mg of beneficial agent formulation at 40° C., wherein the formulation comprised 33.33 wt % (weight percent) porcine somatotropin, 4.53 wt % sodium phosphate monobasic, 28.47 wt % water, 33.0 wt % glycerol, and 0.67 wt % Tween-80. Then, the two subassemblies at their opened ends are joined by inserting partially the second wall section into the first wall section. Finally, 4 drops of moisture-cured cyanoacrylate adhesive are dropped onto the remaining exposed surface, and the members are fully inserted and then twisted to effect a sealed delivery device.

Then, the system is completed by joining the sealed delivery device described above with the protective sleeve. These two are joined by partially inserting the protective sleeve over the glue junction of the sealed system. Next, 4 drops of moisture-cured cyanoacrylic adhesive are dropped onto the remaining exposed surface of the junction, and the sleeve is fully inserted until the molded-in stop on the inside of the protective sleeve is reached. The members are twisted to effect a sealed, fully protected delivery device.

EXAMPLE 2

Two delivery devices with protective sleeves prepared as in Example 1 and five prior art devices that are identical to the two sleeved devices but without the protective sleeve were hydrated for six weeks and were then subjected to a radially applied force of 100 mm/min in an Instron ® at the junction of the water-impermeable and the water-permeable wall portions of the device. The mean maximum load applied to the systems prior to breakage was determined: 2.2 kg$_f$ for the sleeveless systems and 6.2 kh$_f$ for the sleeved systems.

EXAMPLE 3

Delivery devices with protective sleeves were tested in vivo in comparison with prior art devices without sleeves, as follows.

The base of the ear of a finishing hog was disinfected, and a delivery device prepared as in Example 1 either with or without the protective sleeve was implanted into the ear with the orifice of the delivery device oriented up, using a modified trocar implanting device. The hogs were weighed on a weekly basis, and feed intake was monitored. Hogs without any implant served as controls. There were 40 hogs per treatment, and the hogs were held in pens, with 5 hogs per pen. The average daily weight gain was computed, as was feed consumption and feed efficiency. At the end of 6 weeks, the implants were retrieved from the live hogs using local anesthetic. The explanted delivery devices were examined for piston travel (which correlates to the cumulative amount of beneficial agent released) and for overall condition (such as breakage or swelling of the semipermeable membrane). Two separate studies were run, Study I and Study II, and results from these two studies are presented below in Tables A, B and C.

Additional studies following the above procedure were run with unsleeved prior art implants only, and the pooled distribution of delivery rates (correlated from the distance of piston travel) for all the studies (Studies I and II and the prior art implant studies) is presented in Table D below.

The feed efficiency is determined by dividing the pounds of feed consumed by the number of pounds gained.

TABLE A

| 6 WEEK PERFORMANCE RESPONSES - STUDY I | | | |
|---|---|---|---|
| Treatment | Cumulative Avg. Daily Gain | Cumulative Feed Consumption | Cumulative Feed Efficiency |
| Control | 0.71 | 2.77 | 3.91 |
| Without Sleeve | 0.70 | 2.25 (17%) | 3.35 (14%) |
| With Sleeve | | | |
| (0.012 in*) | 0.77 | 2.46 (11%) | 3.21 (18%) |
| (0.020 in*) | 0.74 | 2.34 (16%) | 3.10 (19%) |
| (0.020 in* + holes ) | 0.72 | 2.25 (19%) | 3.08 (19%) |

*thickness of the sleeve wall
holes (or fluid passage means) present in the sleeve wall
percent improvement over the control

TABLE B

| 6 WEEK PERFORMANCE RESPONSES - STUDY II | | | |
|---|---|---|---|
| Treatment | Cumulative Avg. Daily Gain | Cumulative Feed Consumption | Cumulative Feed Efficiency |
| Control | 0.77 | 3.23 | 4.20 |
| Without Sleeve | 0.81 | 2.87 (11%) | 3.55 (15%) |
| With Sleeve (0.020 in)* | 0.81 | 2.73 (15%) | 3.40 (19%) |

*thickness of the sleeve wall
percent improvement over the control

TABLE C

| PHYSICAL CONDITION OF IMPLANTS | | | |
|---|---|---|---|
| Implant | Total Pumps Recovered | % Broken | % Swollen |
| Without Sleeve | | | |
| I* | 39 | 15.4 | 0 |
| II | 35 | 17.1 | 2.8 |
| Total | 74 | 16.2 | 1.4 |
| With Sleeve | | | |
| I | 113 | 0 | 1.3 |
| II | 39 | 0 | 7.7 |
| Total | 152 | 0 | 3.3 |

*Study number

TABLE D

| DISTRIBUTION OF DELIVERY RATES AT 6 WEEKS | | | | | | | | | |
|---|---|---|---|---|---|---|---|---|---|
| Implant | Total Pumps Recovered | Distance of Piston Travel (mm) | | | | | | | |
| | | 0 | 1-5 | 6-10 | 11-15 | 16-20 | 21-24 | 25-29 | ≧30 |
| No Sleeve | 644 | 1.9%* | 2.5% | 2.5% | 3.7% | 5.0% | 5.1% | 70.3% | 9.0% |
| Sleeve | 152 | 0.6% | 0% | 0.6% | 0.6% | 2.6% | 3.3% | 91.4% | 0.6% |

*% of total pumps recovered

The novel devices of this invention use means for the obtainment of precise release rates in the environment of use while simultaneously maintaining the integrity of the device. The protective sleeve according to the invention provides substantially less breakage and malfunction of the delivery devices, with a resulting greatly improved delivery of the beneficial agent. While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. A method for delivering a beneficial agent to an animal, wherein the method comprises:
   (1) admitting into the animal a dispenser comprising:
      (a) a first wall section comprising a wall that surrounds an internal compartment and an open end;
      (b) a second wall section comprising a wall that surrounds an internal compartment and an open end, the wall comprising a composition permeable to the passage of fluid, wherein the open end of the first wall section and the open end of the second wall section are in mated contact;
      (c) a rigid sleeve extending from the first wall section to cover the junction of the first wall section and the second wall section and to at least partially cover the sides of the second wall section, the inside diameter of the sleeve being greater than the outside diameter of the second wall section, and the sleeve being able to resist transient mechanical forces of at least about 2 kilograms force;
      (d) a beneficial agent in the compartment comprising the first wall section;
      (e) at least one expandable driving member in the compartment comprising the second wall section for pushing the beneficial agent from the compartment; and
      (f) exit means for delivering the beneficial agent to the animal;
   (2) allowing fluid to be imbibed through the permeable second wall section of the dispenser for causing the expandable driving member or members to increase in volume; and
   (3) delivering the beneficial agent to the animal by the driving member or members increasing in volume and occupying space in the compartment comprising the first wall section, thereby pushing the beneficial agent through the exit means to the animal.

2. A method according to claim 1 wherein the sleeve resists transient mechanical forces of about 6 kilograms force.

3. A method according to claim 1 wherein the sleeve has a minimum tensile strength of about 9000 psi.

4. A method according to claim 1 wherein the sleeve completely covers the sides of the second wall section and extends to or below the rear end of the second wall section.

5. A method according to claim 1 wherein the sleeve further comprises a plurality of ridges on its inner circumference.

6. A method according to claim 1 wherein the sleeve further comprises a plurality of fluid or fluid vapor passage means.

* * * * *